| United States Patent [19] | [11] Patent Number: 4,891,361 |
| Hatae | [45] Date of Patent: Jan. 2, 1990 |

[54] METHOD OF MINIMIZING ERYTHEMA AND ELASTOSIS

[75] Inventor: Shinkichi Hatae, Ohnojo, Japan

[73] Assignee: Sansho Seiyaku Co., Ltd., Ohnojo, Japan

[21] Appl. No.: 198,637

[22] Filed: May 18, 1988

Related U.S. Application Data

[63] Continuation of Ser. No. 869,746, Jun. 2, 1986, abandoned.

[30] Foreign Application Priority Data

Jul. 2, 1985 [JP] Japan ................................ 60-146029

[51] Int. Cl.$^4$ ........................................... A61K 31/735
[52] U.S. Cl. ................................................... 514/58
[58] Field of Search ................. 549/418; 514/460, 58; 536/103

[56] References Cited

FOREIGN PATENT DOCUMENTS

53-3538  1/1978  Japan ..................................... 424/62
61-109705  5/1986  Japan .

OTHER PUBLICATIONS

Szejtli, "Proceedings of the First International Symposium on Cyclodextrins", Budapest, Hungary, D. Reidel Publ. Co., London, England, 1981, pp. 469–470.

*Primary Examiner*—Nicky Chan
*Attorney, Agent, or Firm*—Jordan and Hamburg

[57] ABSTRACT

Drugs containing, as an effective ingredient, kojic acid or kojic acid/$\beta$-cyclodextrin inclusion complex are effective in preventing elastosis in an animal test using Spraguex-Dawley rats. The drugs also have powerful action to inhibit the formation of melanin, and show an outstanding color fading effect in a culture test using mouse melanoma B16 cells. The drugs have very low toxicity and are externally applied in the form of an ointment, cream, emulsion, pack or solution.

5 Claims, No Drawings

METHOD OF MINIMIZING ERYTHEMA AND ELASTOSIS

This application is a continuation of application Ser. No. 869,746, filed June 2, 1986, now abandoned.

BACKGROUND OF THE INVENTION

1. Field of the Invention

This invention relates to preventive drugs for elastosis containing kojic acid or kojic acid β-cyclodextrin inclusion complex as the effective ingredient, and their method of use.

2. Description of the Prior Art

The human dermis has collagen fiber bundles at its upper layer, and nearly parallel elastic fibers run along or across these collagen fiber bundles, which are evenly distributed over the entire dermal layer.

An increase in the number of elastic fibers and the consequent dissociation and breakage of collagen fiber bundles are often found in exposed parts of the skin of aged persons. This dermal abnormality, called elastosis, causes wrinkles on the skin; and is also known to be closely correlated to the occurrence of malignant carcinomas, particularly senile keratosis, keratoacanthoma, squamous cell carcinoma and basal cell carcinoma, because it is invariably found around these carcinomas.

No drug capable of curing or preventing elastosis has yet been discovered. Such a drug, if developed, would be of great use for protection of the skin and prevention of various skin cancers.

Kojic acid is a compound produced by Aspergillus oryzae or other kojic-acid-producing microorganisms, and many studies have been reported on its applications. These include skin-whitening cosmetics containing kojic acid (Japanese Patent Kokai No.3538/1978), antiinflamatory agents (Japanese Patent Publication No. 34446/1983), ultraviolet preventive agents (Japanese Patent Kokai No.157509/1980), and analgesic agents (Japanese Patent Kokai No.131915/1983).

SUMMARY OF THE INVENTION

We have discovered that kojic acid is effective in preventing elastosis—an effect distinctly different from the skin-whitening, antiinflammatory, analgesic and ultraviolet preventing effects mentioned above. This invention was accomplished based on this finding. Thus this invention relates to preventive drugs for elastosis containing kojic acid or kojic acid/β-cyclodextrin inclusion complex as an effective ingredient. The invention also relates to a method of minimizing erythema and elastosis resulting from UV irradiation comprising applying to skin a composition comprising from 0.1 to 5% by weight of kojic acid included in β-cyclodextrin.

DETAILED DESCRIPTION OF THE PREFERRED EMBODIMENTS

Kojic acid used in this invention is a known compound obtainable by the static or shake culture of a kojic-acid-producing strain belonging to the genus Aspergillus or Penicillium in a liquid culture medium containing glucose or the like as a carbon source.

The kojic acid/β-cyclodextrin inclusion complex used in this invention can be prepared by slowly adding kojic acid to an aqueous suspension of β-cyclodextrin with agitation and by continuing stirring until a clear solution is obtained. The solution of inclusion complex thus prepared may be freeze-dried, as required, for use in the drugs of this invention.

The preventive drugs for elastosis of this invention containing, as an effective ingredient, kojic acid or its inclusion complex with β-cyclodextrin are preferably applied in the form of an ointment, cream, emulsion, pack or solution.

The amount of the effective ingredient contained in said drugs may be varied depending on the type and severity of dermatitis being treated, the spread of the drugs on the affected skin and the frequency of application, but is preferably in the range of from 0.1 to 5% by weight.

The toxicity of kojic acid is extremely low, its $LD_{50}$ for mice and rats (both male and female) being 2.5 to 3.5 g/Kg when it is orally administered. Its safety to the skin is also very high, with no danger of irritation or of causing allergic reaction.

The pharmaceutical preparations of kojic acid or its inclusion complex with β-cyclodextrin can be manufactured by commonly used techniques.

Solutions, for example, may be prepared by dissolving, in pure water, the effective ingredient (kojic acid or its inclusion complex with β-cyclodextrin), a humectant (e.g., glycerol and propylene glycol) and nourishing agents; dissolving preservatives and perfumes in ethanol; and mixing the two solutions obtained above at room temperature to effect solubilization.

Cream can be prepared by dissolving, in pure water, the effective ingredient (kojic acid or its inclusion complex with β-cyclodextrin) and a humectant (e.g., glycerol and sorbitol); mixing solid fatty substances (e.g., beeswax, paraffin wax, microcrystalline wax, ceresin, higher fatty acids and hardened oil), semi-solid fatty substances (e.g., vaselin, lanolin and glycerol), oily substances (e.g., squalane, liquid paraffin and various liquid esters), and oily additives (e.g., preservatives and surface-active agents); gently agitating the aqueous solution obtained above at an elevated temperature; and slowly adding, to this aqueous solution, the oily mixture prepared above and previously heated to the same temperature as the aqueous solution, thereby effecting emulsification.

Emulsions are manufactured by mixing pure water, the effective ingredient (kojic acid or its inclusion complex with β-cyclodextrin), a humectant (e.g. glycerol) and a pH regulator (acid or alkali) at an elevated temperature, followed by addition of ethanol; mixing solid fatty substances (e.g., beeswax and paraffin wax), oily substances (e.g., squalane, liquid paraffin and various liquid esters), and oily additives (e.g., preservatives and surface-active agents) at an elevated temperature; effecting preliminary emulsification by adding the oily mixture to the aqueous solution; and completing emulsification in a homogenizer in the presence of a protective colloid, such as a carboxyl containing vinyl polymer and carboxymethylcellulose.

Packs can be prepared by dissolving, in pure water, the effective ingredient (kojic acid or its inclusion complex with β-cyclodextrin) and a humectant (e.g. glycerol); adding a film-forming agent (e.g., polyvinyl alcohol) to the solution, followed by addition of powdery fillers (e.g., kaolin, talc and zinc oxide), as required; further adding ethanol containing perfume, preservatives and other additives dissolved therein; and kneading the resulting mixture until a homogeneous paste is obtained.

Ointment may be prepared by dissolving, in pure water, the effective ingredient (kojic acid or its inclusion complex with β-cyclodextrin) and a humectant (e.g. glycerol); adding solid fatty substances (e.g., animal and vegetable wax, paraffin wax, ceresin and higher fatty acids), and semi-solid fatty substances (e.g., vaselin and lanolin); and thoroughly kneading the mixture thus obtained.

Typical examples of pharmaceutical preparations of the drugs of this invention are described below.

| Example 1 (Cream) | |
|---|---|
| Kojic acid | 1.0% |
| Polyoxyethylene stearyl ether | 2.09% |
| Polyoxyethylene cetyl ether | 2.91% |
| Beeswax | 4.0% |
| Cetanol | 3.0% |
| Isopropyl palmitate | 2.0% |
| Liquid paraffin | 15.0% |
| Polyethylene glycol monostearate | 0.5% |
| Pure water | 69.4% |
| Methyl p-oxybenzoate | 0.1% |
| Example 2 (Emulsion) | |
| Kojic acid/β-cyclodextrin inclusion complex | 2.0% |
| Self-emulsifiable glycerol monostearate | 1.11% |
| Polyoxyethylene cetyl ether | 1.89% |
| MC stearic acid | 2.0% |
| Cetanol | 1.0% |
| Isopropyl myristate | 2.0% |
| Pure water | 89.90% |
| p-Oxybenzoic acid | 0.1% |
| Perfume | Trace |
| Example 3 (Pack) | |
| Kojic acid | 0.6% |
| Ethanol | 3.0% |
| Methyl p-oxybenzoate | 0.1% |
| Carboxyl-containing vinyl polymer | 1.0% |
| Calcium carbonate | 0.3% |
| Titanium dioxide | 0.02% |
| Pure water | 94.98% |
| Perfume | Trace |
| Example 4 (Solution) | |
| Kojic acid/β-cyclodextrin inclusion complex | 3.0% |
| Ethanol | 10.0% |
| p-Oxybenzoic acid | 0.1% |
| Citric acid | 0.2% |
| Perfume | Trace |
| Pure water | 86.7% |
| Example 5 (Ointment) | |
| Kojic acid | 2.0% |
| Glycerol monostearate | 10.0% |
| Cetanol | 0.5% |
| Stearic acid | 5.0% |
| Lanolin | 2.0% |
| Propylene glycol | 2.0% |
| Liquid paraffin | 3.0% |
| Pure water | 75.5% |

The effects of this invention will be apparent from the results of the animal test described below.

TEST METHOD

Ten heads of female Spraguex-Dawley rats of 4-week age were used for the test. The back of each rat was divided into two zones along its center line; one (test zone) was coated with a 1% suspension of kojic acid in a 1% aqueous solution of carboxymethylcellulose, and the other (control zone) was coated with a 1% aqueous solution of carboxymethylcellulose. The coated solution was washed off with hot water one hour later, and each zone was then irradiated with ultraviolet rays for 20 minutes using four UV tubes (Toshiba, Model 20S;E30) placed 62 cm away from the back of each rat. This operation was performed three times a week (on Monday, Wednesday and Friday) and continued over a period of six months. The drug solution and control solution were applied every day (even on days when UV irradiation was omitted). After that, the coating operation alone was continued for an additional six months.

Severity of erythema developed on each zone was observed immediately after the start of the test, and 2, 4, 6, 8, 10 and 12 months later. The results are summarized in Table 1 below.

TABLE 1

| Month | Zone | Test | Control |
|---|---|---|---|
| Irradiation Period | 0 | — | — |
| | 2 | + | +++ |
| | 4 | ++ | +++ |
| | 6 | ++ | +++ |
| Coating Alone | 8 | — | ± |
| | 10 | — | — |
| | 12 | — | — |

—: No erythema
±: Very slight erythema
+: Slight erythema
++: Medium erythema
+++: Severe erythema At the end of the test, tissues were excised from the test and control zones of each rat, paraffin sections of the skin, prepared from the tissues taken out, were subjected to a Hematoxylin-Eosin, Weigert and Orcein-Giemsa staining process, and the conditions of the elastic fiber were observed. The results are summarized in Table 2 below.

TABLE 2

| Evaluation | Test Zone | Control Zone |
|---|---|---|
| — | 3 | 0 |
| ± | 3 | 0 |
| + | 3 | 0 |
| ++ | 1 | 2 |
| +++ | 0 | 8 |
| Total | 10 | 10 |

—: No elastosis
±: Very slight elastosis
+: Slight elastosis
++: Medium elastosis
+++:Severe elastosis As can be seen from the table, the drugs of this invention are effective in preventing or minimizing the occurrence of elastosis (complete restoration even when slight elastosis was observed). Besides the effects described above, the drugs of this invention also have powerful action to inhibit the formation of melanin. To be more specific, the drugs are very effective in inhibiting the formation of dopachrome (a red pigment). In addition, the drug of this invention containing kojic acid/β-cyclodextrin inclusion complex showed an outstanding effect in a color fading test with mouse melanoma B16 cells. A color fading test of cultured pigment cells was carried out using kojic acid and kojic acid/β-cyclodextrin inclusion complex.

(1) Test Samples

A: Kojic acid
B: 20% solution of kojic acid/β-cyclodextrin inclusion complex (2) Test Method Mouse melanoma B16 cells (hereinafter referred to simply as "B16 cells") (each dish containing 4x10 cells) were grown in Eagle's MEM medium (with 10% fetal calf serum added thereto), (a) in the presence of kojic acid at a concentration of 2.5 mM (Test zone A), (b) in the presence of kojic acid/β-cyclodextrin inclusion complex at a concentration of 2.5 mM (as kojic acid) (Test zone B), and (c) in the absence of any drug (Test zone C), at 37° C. for six days in an atmosphere consisting of 5% $CO_2$ and 95% air. At the end of incubation, each culture was treated with trypsin, then centrifuged at 2000rpm for five minutes to prepare cell pellets, and the degree of blackness was visually compared.

(3) Result

Considerable color fading was observed with Test zone A, compared with Test zone C (control). Marked fading was noticed with Test zone B (by far the more marked than Test zone A), the color of the pellet being white to faint yellow.

The above test result clearly shows the outstanding effect of kojic acid and kojic acid/β-cyclodextrin inclusion complex (the effective ingredients of the drugs of this invention) to inhibit the formation of melanin.

What is claimed is:

1. A method of minimizing erythema or elastosis resulting from UV irradiation comprising applying to skin a composition comprising from 0.1 to 5% by weight of kojic acid included in β-cyclodextrin.

2. A method according to claim 1, wherein the composition is applied in a form selected from the group consisting of an ointment, a cream, an emulsion, a pack and a solution.

3. A method according to claim 1, wherein the composition further comprises a humectant.

4. A method according to claim 3, wherein the humectant is selected from the group consisting of glycerol, propylene glycol, sorbitol and mixtures thereof.

5. A method according to claim 1, wherein the composition is applied periodically.

* * * * *